United States Patent [19]

Haishi et al.

[11] Patent Number: 5,093,099
[45] Date of Patent: Mar. 3, 1992

[54] FLAKY POWDER OF ZINC OXIDE AND ITS COMPOSITION FOR EXTERNAL USE

[75] Inventors: Tomoyuki Haishi, Osaka; Emi Sakamoto, Wakayama; Hiroshi Itoh, Tokyo, all of Japan

[73] Assignee: Kao Corporation, Tokyo, Japan

[21] Appl. No.: 270,046

[22] Filed: Nov. 14, 1988

[30] Foreign Application Priority Data

Nov. 16, 1987 [JP] Japan .................. 62-288665
Dec. 28, 1987 [JP] Japan .................. 62-335853

[51] Int. Cl.$^5$ .................. C01G 9/02; A61K 33/32; A61K 7/021; A61K 7/035
[52] U.S. Cl. .................. 423/622; 423/101; 423/102; 424/641; 424/642; 424/63; 424/69; 514/844
[58] Field of Search ............ 423/622, 101, 102, 103, 423/104, 106, 105; 424/641, 642, 63, 69; 106/425; 514/844, 848

[56] References Cited

U.S. PATENT DOCUMENTS

| | | | |
|---|---|---|---|
| 3,453,072 | 7/1969 | Vian-Ortuño | 423/104 |
| 4,255,418 | 3/1981 | Bailey | 424/642 |
| 4,261,965 | 4/1981 | Fukuda et al. | 423/544 |
| 4,512,978 | 4/1985 | Inwood | 424/642 |
| 4,544,761 | 10/1985 | Taylor et al. | 514/844 |
| 4,603,047 | 7/1986 | Watanabe et al. | 4524/69 |
| 4,713,242 | 12/1987 | Trenzeluk | 424/642 |
| 4,772,331 | 9/1988 | Noguchi et al. | 424/69 |
| 4,842,848 | 6/1989 | Saita et al. | 424/69 |

FOREIGN PATENT DOCUMENTS

| | | | |
|---|---|---|---|
| 572977 | 3/1959 | Canada | 423/106 |
| 0273089 | 7/1988 | European Pat. Off. . | |
| 1443462 | 1/1971 | Fed. Rep. of Germany | 423/622 |
| 2375904 | 9/1978 | France . | |
| 0116296 | 10/1978 | Japan | 423/622 |
| 53-116296 | 10/1978 | Japan . | |
| 54-019237 | 7/1979 | Japan . | |
| 54-115698 | 9/1979 | Japan | 423/622 |
| 0042282 | 3/1980 | Japan | 423/622 |
| 57-149827 | 9/1982 | Japan . | |
| 0149827 | 9/1982 | Japan | 106/425 |
| 0205319 | 12/1982 | Japan | 423/101 |
| 0209824 | 12/1982 | Japan | 423/101 |
| 62-270409 | 11/1987 | Japan | 423/622 |
| 2260716 | 11/1987 | Japan | 423/622 |
| 62-335853 | 12/1987 | Japan | 423/622 |

Primary Examiner—Michael Lewis
Assistant Examiner—Steven Bos
Attorney, Agent, or Firm—Flynn, Thiel, Boutell & Tanis

[57] ABSTRACT

Flaky fine particles of zinc oxide have an average particle diameter of 0.1 to 1 micron, an average particle thickness of 0.01 to 0.2 micron and a mean platy ratio (aspect ratio) of at least 3. They are useful as an ingredient for an external composition containing a medicine or cosmetic.

7 Claims, 4 Drawing Sheets

1μ

1μ

FLAKY POWDER OF ZINC OXIDE AND ITS COMPOSITION FOR EXTERNAL USE

FIELD OF THE INVENTION

The present invention relates to zinc oxide powder mainly comprising flaky particles and a process for producing these zinc oxide particles in an easy manner.

The term "flaky particles" herein indicates platy, sheet, hexagonalplaty, discoid, tabular, foliar, micaceous and foil-shaped particles, excluding aggregates of them.

The present invention relates to external preparations such as cosmetics and medicines for external use containing flaky zinc oxide particles, which have a high adhesion to the skin and excellent ultraviolet absorptivity and bring about a comfortable finish and feeling during use.

PRIOR ART

Zinc oxide is produced on an industrial scale usually by a process wherein metallic zinc is burnt by heating in air. Although granular and acicular particles can be thus produced, no powder comprising flaky particles has been directly produced thereby as yet.

An indirect process for producing platy skeletal zinc oxide particles was disclosed in Japanese Patent Laid-Open No. 82698/1978 which comprised slowly adding an alkali to an aqueous zinc salt solution at a high temperature while the pH of the solution was kept in an acidic region of 4.5 to 6 to form basic zinc hydroxide in the form of hexagonal platy particles having a large particle diameter and treating them at 900° C. for 1 h. However, flaky zinc oxide particles having an average particle diameter of 1 $\mu$m or less as disclosed in the present invention could not be produced by this process.

Although it was referred to in the above-described Japanese Patent Laid-Open No. 82698/1978 that fine particles having an average particle diameter of 1 $\mu$m or less could be produced by making a zinc nitrate solution weakly alkaline, the product thus obtained was zinc hydroxide in the form of an aggregate of fine foil-shaped particles. Thus, even if the product is dehydrated and converted into zinc oxide, the aggregate cannot be disintegrated into particles.

The behavior of such giant particles and aggregated particles are widely different from those of the flaky particles from the viewpoint of the powder properties such as orientation, compaction and optical properties. Therefore, improvement in the characteristics of zinc oxide and expansion of the uses thereof were restricted.

Zinc oxide is usually used as a white pigment for cosmetics and an antiinflammatory astrigent for medicines. Recently, it was found that fine particles of zinc oxide having an average particle diameter of 0.07 to 0.3 $\mu$m were effective as an ultraviolet absorber, particularly for absorbing rays in the UV-A region, and they are practically used for this purpose.

However, when the fine zinc oxide particles are used in a large amount in order to obtain a high ultraviolet shielding effect, the users' feeling and the finish are impaired. Namely, in such a case, users will realize a squeaky touch and the covering effect thereof is increased excessively to make it impossible to obtain a natural finish. The amount of the zinc oxide particles usable is thus limited.

The present invention has been completed under these circumstances. An object of the present invention is to provide zinc oxide powder in the form of flaky particles having a specific diameter which could not be produced in the prior art. In particular, the object of the present invention is to produce zinc oxide powder having superior particle orientation, adhesion to a base or substrate, ultraviolet shielding properties and electrical conductivity by a simple process at a low cost.

After intensive investigations made for the purpose of solving the problems of the prior art, the inventors have found that these objects can be attained by precipitating zinc oxide from a specifically prepared mother liquor in the production of zinc oxide directly from an aqueous solution of a zinc salt. The present invention has been completed on the basis of this finding.

The invention provides flaky fine particles of zinc oxide having an average particle diameter of 0.1 to 1 micron, an average particle thickness of 0.01 to 0.2 micron and a mean platy ratio (aspect ratio) of at least 3.

The invention also provides two processes for preparation of the zinc oxide. The first process for preparing flaky fine particles of zinc oxide defined above comprises the step of forming precipitates in a mother liquid which (a) contains zinc ions, (b) one or more acid radicals in a total amount exceeding the equivalent with respect to the zinc ion and (c) has a pH of 11 or higher and separating them from the liquid. The second process for preparing flaky fine particles of zinc oxide defined above comprises the steps of mixing an aqueous solution of a zinc salt with a solution of a precipitating agent, agitating well and forming precipitates in a mother liquid of the resulting mixture having (a) a zinc concentration of 15 wt. % or smaller as zinc oxide and (b) a pH of 11 or larger.

The invention further provides a zinc oxide composition for external use to the human body, which comprises the flaky fine particles of zinc oxide as defined above and a base for a cosmetic or medicine.

The present invention provides zinc oxide powder mainly comprising flaky fine particles having an average particle diameter of 0.1 to 1 $\mu$m, an average particle thickness of 0.01 to 0.2 $\mu$m and a mean platy ratio of at least 3. The present invention provides also a process for producing zinc oxide powder mainly comprising flaky fine particles having an average particle diameter of 0.1 to 1 $\mu$m, and average particle thickness of 0.01 to 0.2 $\mu$m and a mean platy ratio of at least 3 directly from an aqueous solution of a zinc salt, characterized in that a precipitate is formed from a mother liquor which:
  (a) contains zinc ions,
  (b) contains one or more acid radicals in a total amount exceeding the equivalent with respect to the zinc ion, and
  (c) has a pH of 11 or higher.

The present invention provides an external preparation having a high adhesion to the skin and an excellent ultraviolet absorptivity and capable of providing a comfortable finish and feeling, which is characterized by comprising flaky zinc oxide having an average particle diameter of 0.1 to 1 $\mu$m, an average particle thickness of 0.01 to 0.2 $\mu$m and a mean platy ratio of at least 3.

The average particle diameter, average particle thickness and mean platy ratio herein are determined by methods described in the Examples given below.

In the process of the present invention, zinc ions are reacted with the alkali solution at a reaction temperature of 60° C. or below, preferably 40° C. or below, under violent stirring in a short period of time. The acid radical(s) contained in the mother liquor is(are), for example, $NO_3^-$, $SO_4^{2-}$, $CH_3COO^-$, $Cl^-$, $PO_4^{3-}$, $CO_3^{2-}$ and/or $C_2O_4^{2-}$. The mother liquor must contain the acid radical(s) in an amount exceeding the equivalent with respect to the zinc ion and have a pH of at least 11, preferably at least 12.

When a white slurry formed by the precipitation is heated to 60° to 100° C., preferably 90° to 100° C., and kept at that temperature for at least 10 min, preferably at least 30 min, flaky zinc oxide having an improved crystallizability is formed.

Now the description will be made on the characteristic features of the present invention. When the amount of the acid radical is less than the equivalent with respect to the zinc ion, zinc oxide thus formed mainly comprises flaky, aggregated crystals and, therefore, the control of the conditions in order to form the flaky particles intended in the present invention is quite difficult. Although the upper limit of the amount of the acid radical is not particularly provided, an extremely excessive amount thereof, relative to the zinc ion, is impractical since a troublesome washing operation would be necessary for the particles isolation. Although the preferred amount of the acid radical varies, depending on the kind of the acid radical ion, it is preferably 1.05 to 2 equivalents per equivalent of the zinc ion for obtaining preferred results.

A pH lower than 11 is unfavorable for the present invention, because zinc hydroxide is formed or the product is in the form of granules or grains at such a pH condition.

When the reaction temperature is higher than 60° C., the platy crystals cannot be formed, even at a pH of 11 or higher, and the product unfavorably mainly comprises globular or massive crystals. However, it was confirmed from the results of powder X-ray diffractiometry that when a white slurry of flaky crystals, formed at a reaction temperature of lower than 60° C., is heat-treated at 60° C. or higher, the crystallizability is improved while the shape is kept as it is.

The powdery product is isolated by filtration followed by washing. When a water-soluble organic solvent is used for washing in the final step, the subsequent drying and pulverization operations are facilitated. This is particularly effective when a high bulk specific volume is intended.

The acid radical in an amount exceeding the equivalent with respect to the zinc ion is added in the form of a corresponding acid or salt to either the zinc salt solution or alkali solution. The salts are water-soluble, such as sodium sulfate, sodium nitrate, sodium chloride, sodium acetate, potassium sulfate, sodium phosphate, sodium oxalate and sodium carbonate. The usable alkalis include, for example, sodium hydroxide, potassium hydroxide, lithium hydroxide and ammonium hydroxide.

The aqueous zinc salt solution and the alkali are added by pouring, or adding dropwise, the alkali into the zinc salt solution or vice versa or, alternatively, both of them are simultaneously poured in or added dropwise to water or the salt solution.

It was confirmed by X-ray diffractometry that the flaky zinc oxide thus formed was crystalline. This product has a quite high bulk specific volume due to the particle shape thereof. The product had a bulk specific volume of, surprisingly, several to ten-odd times that of zinc oxide produced by an ordinary gas phase process.

According to ultraviolet spectroscopy, the product has an ultraviolet absorptivity higher than that of commercially available zinc oxide and a visible light absorptivity lower than that of the latter. Namely, the product behaves as a highly transparent, characteristic ultraviolet absorber.

The flaky powder of zinc oxide of the invention can be produced by another process, the second process defined above.

The precipitating agent to use in the invention includes water-soluble acids and water-soluble bases which can form precipitates of zinc oxide or zinc hydroxide, preferably with a production yield of 50 percent by weight or higher, when it reacts with the zinc salt contained in the solution. It preferably includes sodium hydroxide, aqueous ammonia, ethanolamines and sodium acetate for use with an acidic solution of a zinc salt such as zinc nitrate, zinc sulfate and zinc acetate. It preferably includes sulfuric acid, nitric acid, hydrochloric acid, acetic acid, oxalic acid, citric acid, succinic acid and carbonic acid for use with a basic solution of a zinc salt such as sodium zincate.

In the mixing step, any conventional agitator may be used, preferably including one that provides for Reynolds number of 30 or larger, preferably from 100 to 100,000. It is important to agitate the mixture thoroughly. Reynolds number may be defined in a conventional way, for example, calculated by the equation:

$$(\text{diameter of agitator})^2 \times (\text{the number of rotation}) \times$$
$$(\text{density of solution mixture})/(\text{viscosty of the solution mixture})$$

Weaker agitation could result in aggregation of the zinc flakes and too strong agitation would result in some loss of energy.

It is preferable to add the precipitating agent to the mixture while it is being stirred, more preferable within a period of time ranging from 1 second to 15 minutes from the commencement of mixing. Most preferable addition is made within 1 to 5 minutes. Longer time taken for the addition would provide aggregation of the crystals. Anyhow, a balance is required between quick addition of the precipitating agent and sufficient agitation of the mixture. The above defined agitation should be made at the same time both solutions are mixed with each other. The crystals can be formed without the agitation continuing further.

There is no rule on the order of addition of the zinc salt solution and the precipitating agent. It is preferable to add the precipitating agent to the zinc salt solution or conduct addition of both.

It is essential that the mixture have a zinc salt concentration of 15 wt. % or smaller. A larger content would produce aggregation of the crystals. A smaller one simplifies the control of the form of powder. A range from 15 to 0.1 wt. % is proposed from the practical point of view.

In both first and second processes for preparation of zinc powder according to the invention, the use of the water-soluble organic substance renders easier production of the intended form of zinc oxide. It includes alcohols such as aliphatic alcohols having 1 to 6 carbon atoms, such as methanol, ethanol, propanol, butanol, pentanol and hexanol, polyols such as aliphatic polyhydric alcohols including propanediol, butanediol, heptanediol, ethylene glycol, glycerin and polyethylene glycol, phenol, phenol derivative having C1 to C5 substituent such as cresol, catechol, catechol having a substituent of C1 to C5 alkyl, heterocyclic alcohols such as furfuryl alcohol, C1 to C6 ketones such as acetone, acetylacetone, methylethylketone and lactone, ethers such as ethylether, tetrahydrofurane, dioxane and polyoxyethylenealkylether, ethers such as ethylene oxide or propylene oxide adducts and polyethers, esters such as ethyl acetate, ethyl acetoacetate and ethyl esters of glycine, carboxylic acids such as formic acid, acetic acid, oxalic acid, citric acid, tartaric acid, salicylic acid, benzoic acid, malonic acid, acrylic acid, maleic acid, succinic acid, propionic acid, glycerolic acid, eleostearic acid, polyacrylic acid, polymaleic acid and a copolymer of acrylic acid and maleic acid, polycarboxylic acids, hydroxycarboxylic acids, salts of carboxylic acids and polycarboxylic acids, celluloses and saccharides such as carboxymethyl celluloses, glucose, galactose, sucrose, lactose, amylose and chitin, ureas such as urea and acetylurea, sulfonates such as alkylbenzenesulfonate, para-toluenesulfonate, alkylsulfonate, alpha-olefinsulfonate, polyoxyethylenealkylsulfonate, ligninsulfonate and naphthalenesulfonate, amino acids such as glycine, glutamic acid, aspartic acid and alanine and amines such as hydroxylamines such as monoethanolamine, diethanolamine, triethanolamine and butanolamine, trimethylaminoethylalkylamine, alkylpyridium sulfate, alkyltrimethylammonium halide, alkylbetaine and alkyldiethylenetriamino acetic acid.

It is more advantageous to add the water-soluble organic substance or an inorganic salt thereof to a mother liquid having a pH of 11 or larger.

In both first and second processes for preparation of the zinc oxide, the following further treatment improves production of the zinc oxide. The white slurry containing precipitates of zinc oxide is heated up to 60° to 100° C., preferably from 90° to 100° C., for 10 minutes or longer, preferably for 30 minutes or longer, to obtain zinc oxide by better crystallization. Then, the powder is separated from the slurry by filtration and washing and then washing the powder by using a water-soluble organic solvent to render easier the subsequent drying and pulverization steps. This washing is useful when zinc oxide having a large apparent specific volume is obtained.

As described above, zinc oxide powder, having useful characteristics by virtue of its form, i.e. flaky particles, which could not be produced by the prior art and usable as a quite characteristic industrial material can be obtained.

The zinc oxide powder obtained by the present invention is usable as a material for white pigments, medicines, rubbers, plastic fillers, cosmetics, catalysts, electrochemical materials, glasses and ceramics. Further, since the zinc oxide of the present invention is in the form of flaky particles, it exhibits high ultraviolet absorptivity, photoconductivity and surface adhesion when applied by coating or pressing, so that it can exhibit excellent performance when used as a material for cosmetics, electronic materials, oriented ferrite, fluorescent substances and paper making fillers. The product of the present invention thus has a remarkably high industrial value.

The flaky zinc oxide of the present invention can be incorporated as is in the external preparation or, if necessary, it can be made water-repellent by, for example, a silicone treatment before its incorporation.

The amount of the flaky zinc oxide in the external preparation, which varies depending on the kind of the external preparation, is preferably in the range of 0.1 to 50 wt. %, particularly 1 to 25 wt. %.

The external preparation of the present invention is usable as a cosmetic, such as powdery foundation, creamy foundation, oily foundation or cream, or an external medicine such as an ointment.

The external preparation of the present invention can be produced by mixing the flaky zinc oxide with an ordinary cosmetic base or external medicine in an ordinary manner.

The bases usable herein include powdery bases such as extenders, e.g. mica, talc, sericite, kaolin and nylon powder; inorganic pigments, e.g. titanium oxide, zinc flower, iron oxide and pearl; and organic pigments, e.g. Red Pigment 202, Red Pigment 226, Yellow Pigment 4 and aluminum lake. Powders subjected to a water-repellent surface treatment by a known method such as silicone treatment, metallic soap treatment or N-acrylglutamic acid treatment can also be used. The oils usable herein include hydrocarbons such as solid and liquid paraffin, crystal oil, ceresine, ozocerite and montan wax; vegetable oils, animal oils and fats and waxes such as olive oil, earth wax, carnauba wax, lanolin and spermaceti; fatty acids and esters of them such as stearic acid, palmitic acid, oleic acid, glycerol monostearate, glycerol distearate, glycerol monooleate, isopropyl myristate, isopropyl stearate and butyl stearate; and alcohols such as ethyl alcohol, isopropyl alcohol, cetyl alcohol, stearyl alcohol, palmityl alcohol and hexyldodecyl alcohol. Further polyhydric alcohols having a humectant effect, such as glycol, glycerol and sorbitol, are also usable.

A known UV-B absorber can be incorporated in the external preparation of the present invention. The UV-B absorbers usable herein include, for example, p-methylbenzylidene-D,L-camphor, its sodium sulfonate, sodium 2-phenylbenzimidazole-5-sulfonate, sodium 3,4-dimethylphenylglyoxylate, 4-phenylbenzophenone, isooctyl 4-phenylbenzophenone-2'-carboxylate, p-methoxycinnamates, 2-phenyl-5-methylbenzoxazole and p-dimethylaminobenzoates. Further the preparation may contain a thickening agent, antiseptic, antioxidant, etc. as is usually contained in external preparations.

The external preparation of the present invention comprising the flaky zinc oxide has a high adhesion to the skin and excellent ultraviolet absorptivity and provides a comfortable finish and feeling during use. Particularly, when it is used as a cosmetic, it exhibits characteristic features such as a high adhesion to the skin, maintenance of make up, transparent beautiful finish, comfortable feel during use and high ultraviolet absorptivity.

EXAMPLES

The following examples will further illustrate the present invention, which by no means limit the technical applicability of the present invention.

The methods and conditions for the determination of the characteristics in the following Examples and Comparative Examples will now be described. A commercially available fine zinc flower or zinc white (particle diameter is 270 nm) was used as the comparative sample.

(1) Bulk specific volume

The bulk specific volume was determined according to JIS Z 2504.

(2) Adhesion to a base or substrate 0.5 g of the sample was ultrasonically dispersed in 100 g of acetone and a slide glass was dipped therein and then dried to form a thin film on the glass base. The film was scraped off with a small spatula to qualitatively determine the adhesion thereof.

(3) Ultraviolet absorptivity

The sample was suspended in glycerol and the absorbance thereof at 700 to 300 nm was determined with a spectrophotometer (UV-265; a product of Shimadzu Corporation) to evaluate the light transmittances in the ultraviolet and visible ray regions.

(4) Average particle diameter and mean platy ratio

The average particle diameter was determined by repeatedly determining the average volume of 20 particles taken at random from a random field of view in a transmission electron micrograph. The average particle diameter of elliptic particles was given in terms of the arithmetical means of the major axis and the minor axis. The mean platy ratio was given in terms of the ratio of average particle diameter to average particle thickness, with the fractions being rounded off to the nearest whole number, wherein the average particle thickness was determined by the arithmetic mean of the thicknesses of all the measurable particles in the above-described fields of view in the transmission electron micrograph.

(5) Particle size distribution

The particle size distribution was determined by centrifugal sedimentation with CAPA 500 (a product of Horiba Seisakusho).

(6) X-ray diffraction

The X-ray diffraction was determined by using Cu Kα rays with Rotaflex PL 200 (a product of Rigaku Denki Co.).

EXAMPLE 1

300 g of a 2 molal solution of zinc nitrate and 20 g of sodium sulfate were added to 1 l of ion-exchanged water. 700 g of 2N NaOH was poured into the mixture and maintained at 30° C. under violent stirring. The pH of the mixture immediately after the addition was 12.3. The slurry thus formed was left to stand for 30 min to age, then heated at 100° C. for 1 h, filtered and washed. A wet cake thus formed was left to dry at 110° C. to a constant weight and then pulverized to obtain a white powder.

Figure 1:
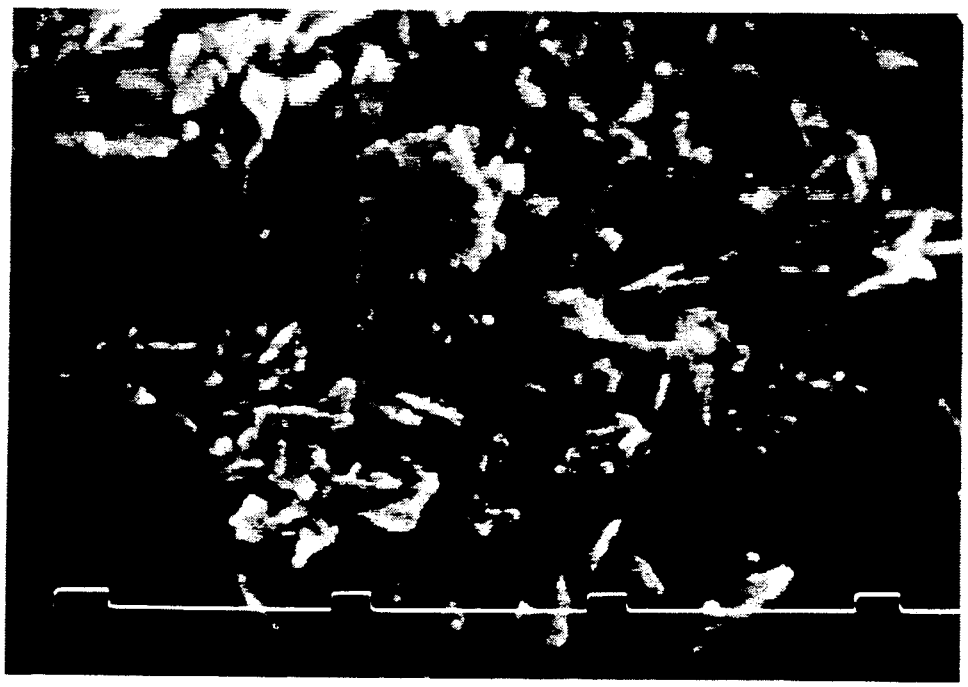
FIG. 1 is a scanning electron photomicrograph of the particle structure of the flaky zinc oxide obtained in Example 1.
Figure 4:
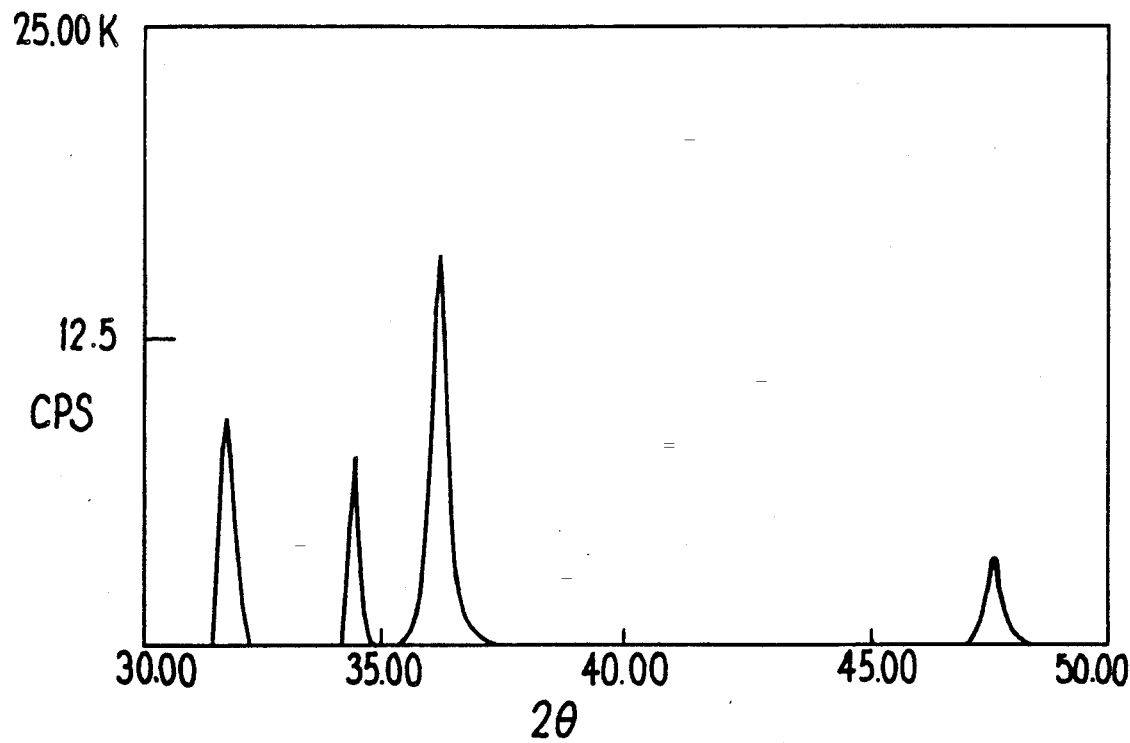
FIG. 4 is an X-ray diffraction pattern of zinc oxide powder obtained in Example 1.

The powder was identified according to powder X-ray diffractometry by an ordinary method to obtain the results shown in FIG. 4. From the results, the product was identified as zinc oxide. According to observation with a scanning electron microscope (SEM), it was a powder mainly comprising independent flaky particles having an average particle diameter of 1 μm or less and free from any aggregation as shown in FIG. 1.

A film was formed from the product in the above-described manner and the adhesion thereof to a base was determined to reveal that the adhesion thereof was far stronger than that of a comparative zinc oxide film formed in the same manner as above.

The loose bulk specific volume of the product was 12 cc/g, which was surprisingly higher than that of the comparative zinc oxide (1 to 2 cc/g). In the spectroscopic analysis of the powder, a particularly excellent absorbance was observed at λmin of 363 nm unlike the comparative sample as shown in Table 1. The absorbance of the product in the visible region was lower than that of the comparative sample to indicate that the product was highly transparent.

Figure 3:
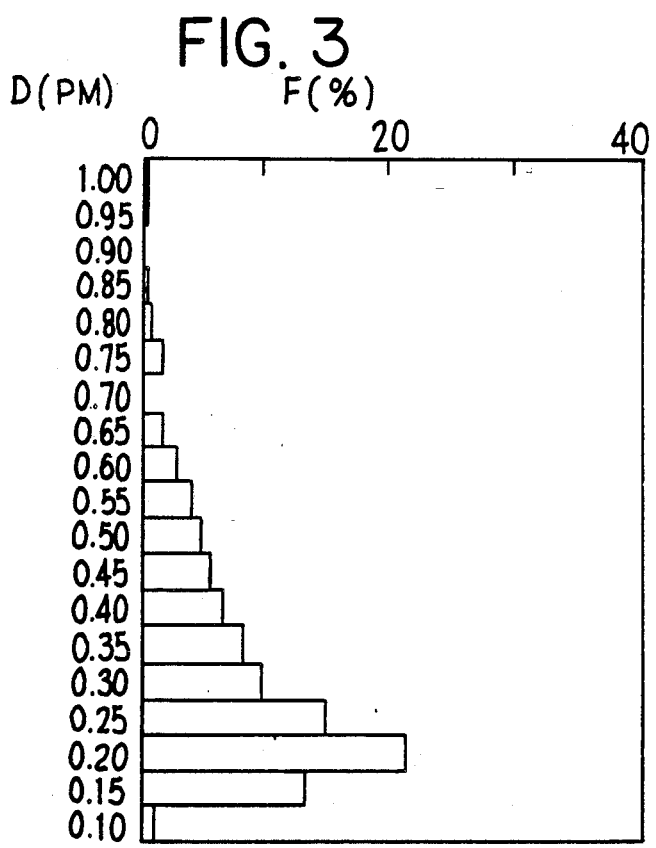
FIG. 3 shows the results of the determination of the particle size distribution of the zinc oxide powder produced in Example 1 by centrifugal sedimentation.

The particle size distribution of the powder determined by centrifugal sedimentation was as shown in FIG. 3.

EXAMPLES 2 TO 7

Flaky zinc oxide powders were prepared in the same manner as that of Example 1 except that zinc nitrate was replaced with zinc acetate (Example 2), the amount of sodium sulfate was reduced to a half (Example 3) or a quarter (Example 4), the zinc ion concentration was doubled (Example 5), sodium sulfate was replaced with sodium chloride (Example 6) and the amounts of ion-exchanged water and 2N NaOH added were 400 ml and 680 g, respectively (Example 7).

The results of the determination are shown in Table 1.

TABLE 1

| Example | Average particle diameter μm | Mean platy ratio | UV absorbance λ = 363 nm T % | Apparent bulk specific volume cc/g |
|---|---|---|---|---|
| 1 | 0.38 | 10 | 28 | 12 |
| 2 | 0.20 | 8 | 25 | 8 |
| 3 | 0.34 | 10 | 28 | 10 |
| 4 | 0.52 | 9 | 32 | 5 |
| 5 | 0.43 | 8 | 27 | 7 |
| 6 | 0.62 | 9 | 31 | 6 |
| 7 | 0.88 | 7 | 33 | 4 |

COMPARATIVE EXAMPLE 1

The same procedure as that of Example 1 was repeated except that the amount of 2N NaOH was 650 g. The pH was 10.8 and the loose bulk specific volume of the obtained powder was 1 cc/g. A subsequent treatment was conducted in the same manner as above. The powder was observed with SEM to find that it comprised fine granular particles having an average particle diameter of 0.2 μm. The ultraviolet absorbance thereof was 30%.

COMPARATIVE EXAMPLE 2

Figure 2:
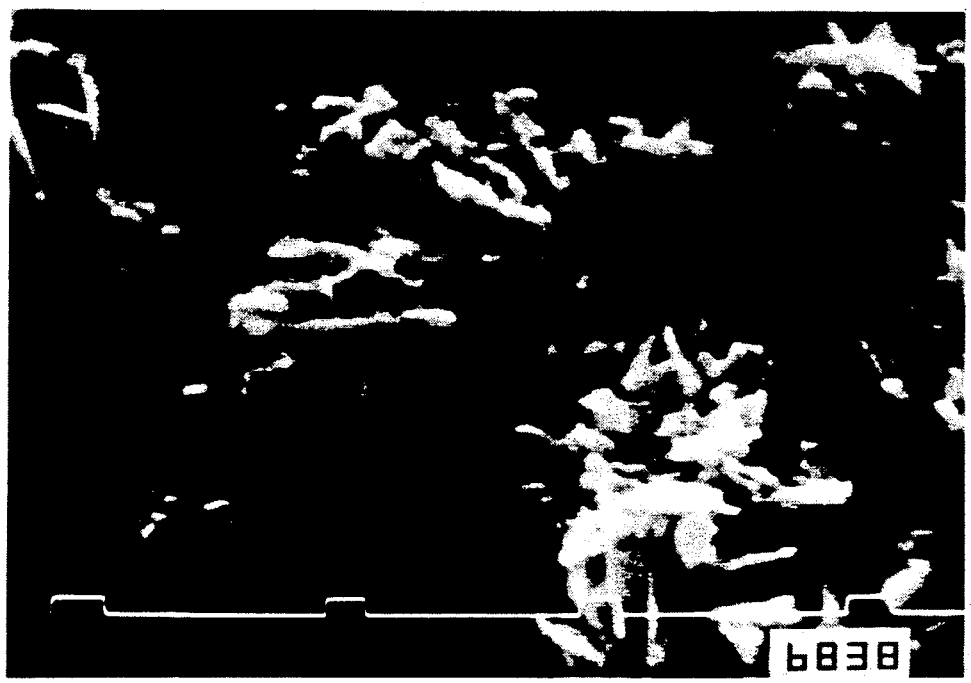
FIG. 2 is a scanning electron photomicrograph of the particle structure of aggregated flaky zinc oxide obtained in Comparative Example 2.

Zinc oxide powder was prepared as in Example 1 except that no sodium sulfate was added. The powder was observed with SEM to find that it comprised an aggregate of fine crystalline zinc oxide particles as shown in FIG. 2. The average particle diameter, ultraviolet absorbance and loose bulk specific volume of the product were 0.4 μm, 34% and 3 cc/g, respectively.

EXAMPLE 8

Figure 5:
FIG. 5 is a transmission electron microscope (TEM) picture of zinc oxide obtained in Example 8.

300 grams of 2 mole percent solution of zinc sulfate was added to 1 liter of ion-exchanged water. The mixture was allowed to stand at 30° C. and then 700 g of 2N-NaOH solution was added thereto over a period of 20 seconds with agitation at 1000 rpm or higher by turbine wings having a diameter of 8 cm. The mixture was found to have a pH of 12.3 just after the addition. The slurry was allowed to age for 30 minutes and then heated at 100° C. for 1 hour. A wet cake was obtained from the slurry with filtration and washing and was allowed to be dried until it reached a constant weight. Then it was pulverized into white powder. The powder was identified with zinc oxide in the same way as shown in Example 1. Then it was observed with a transmission electron microscope (TEM) and was found to mainly comprise independent flaky particles having an average particle size of 1 micron or smaller, without aggregation. FIG. 5 shows a picture of the zinc oxide.

Figure 7:
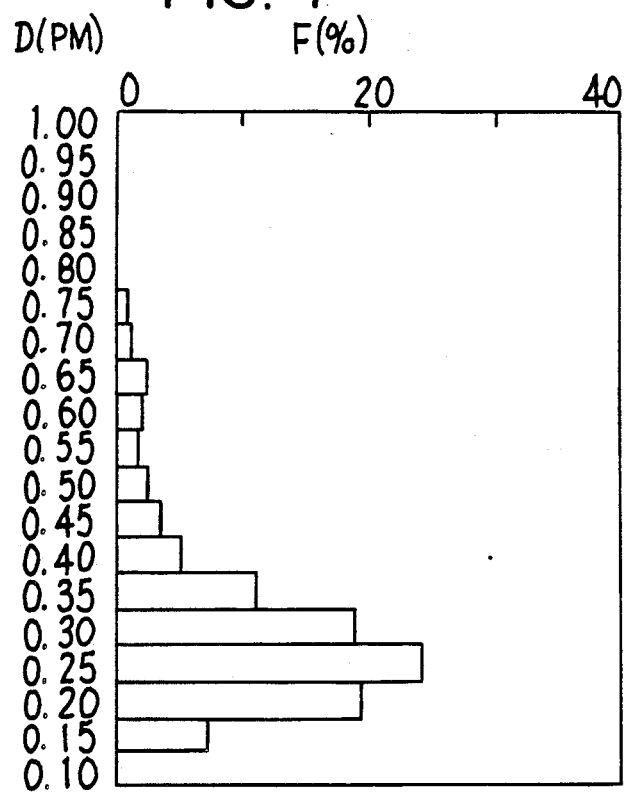
FIG. 7 shows a size distribution of zinc oxide obtained in Example 8, determined by the centrifugal sedimentation method.
Figure 8:
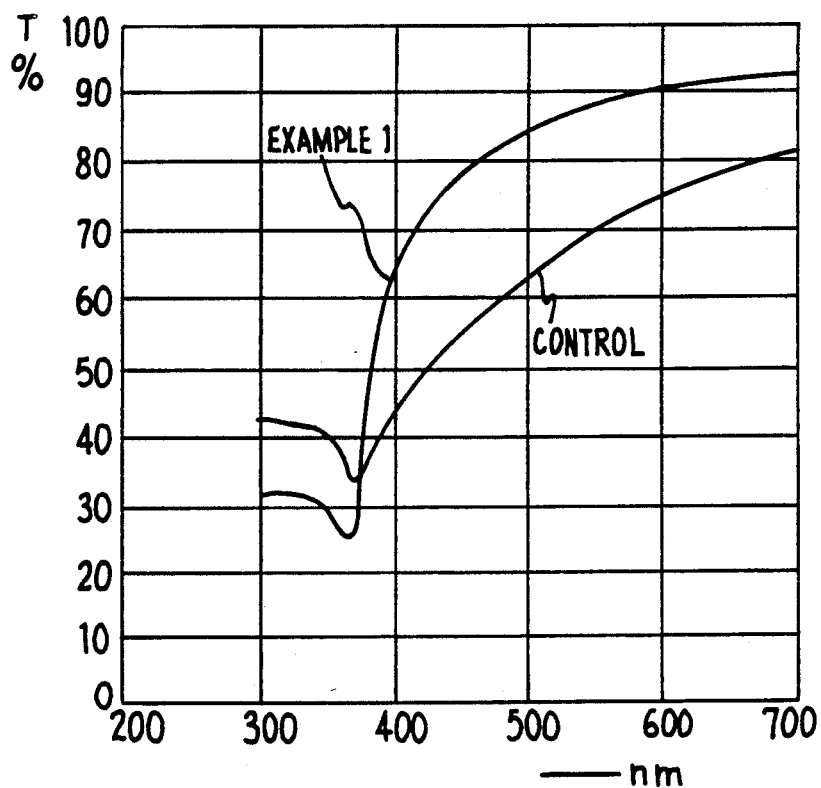
FIG. 8 is a visual, UV spectrum of zinc oxide obtained in Example 1 and a control.

A film was prepared from the zinc oxide and tested in the same manner as shown in Example 1 and was found to be much stronger than the control. It was found to have a loose bulk specific volume of 12 cc/g and to have an intensive absorption at 363 nm as shown in Table 2. It had a lower absorption in the visible region than the control and was found to be improved in transparency. FIG. 7 shows a result of a size distribution of the zinc oxide according to the centrifugal segmentation method.

EXAMPLES 9 to 10

Zinc oxide was obtained in the same way as shown in Example 8, except for using zinc nitrate in Example 9 and zinc acetate in Example 10 instead of zinc sulfate, having the same shape as in Example 8.

EXAMPLES 11 to 16

Zinc oxide was obtained in the same way as shown in Example 8, having the same shape as in Example 8, except that 400 ml of ion-exchanged water was used and the solution of zinc sulfate contained 1 g of tartaric acid in Example 11, 1 g of oxalic acid in Example 12, 10 g of salicyclic acid in Example 13, 1 g of citric acid in Example 14, 1 g of malonic acid in Example 15 and 10 g of lignin sulfonate in Example 16.

EXAMPLE 17

Zinc oxide was obtained in the same way as shown in Example 8, except that the solution of zinc sulfate contained 20 g of sodium sulfate and a 2N sodium hydroxide solution contained Poise 530 (tradename), having a fine size and improved dispersing property.

TABLE 2

| Example | average particle diameter | mean platy ratio | UV absorbance at 363 nm T % | apparent bulk specific volume cc/g |
| --- | --- | --- | --- | --- |
| 8 | 0.42 | 12 | 26 | 12 |
| 9 | 0.45 | 10 | 28 | 11 |
| 10 | 0.48 | 14 | 27 | 10 |
| 11 | 0.65 | 15 | 31 | 9 |
| 12 | 0.63 | 13 | 30 | 7 |

TABLE 2-continued

| Example | average particle diameter | mean platy ratio | UV absorbance at 363 nm T % | apparent bulk specific volume cc/g |
| --- | --- | --- | --- | --- |
| 13 | 0.59 | 18 | 26 | 10 |
| 14 | 0.64 | 11 | 27 | 5 |
| 15 | 0.68 | 12 | 33 | 6 |
| 16 | 0.72 | 15 | 28 | 8 |
| 17 | 0.34 | 10 | 25 | 7 |

COMPARATIVE EXAMPLE 3

Zinc oxide was obtained in the same manner as shown in Example 8 except that 650 g of 2N sodium hydroxide solution was used. The mixture was found to have a pH of 10.8, but also had a loose bulk specific volume of 1 cc/g, a size of 0.2 micron and a UV absorbtion of 30 percent.

COMPARATIVE EXAMPLE 4

Figure 6:
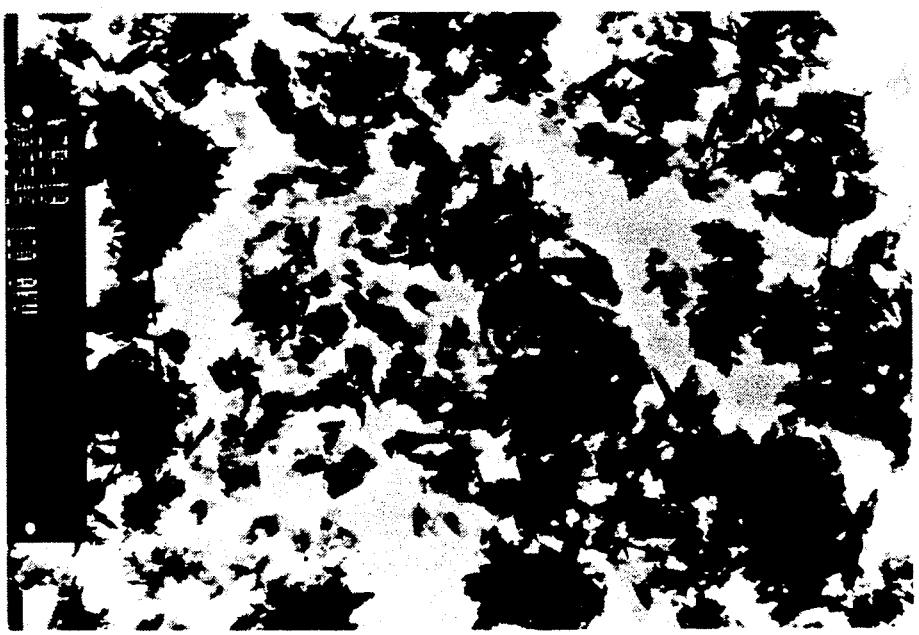
FIG. 6 is a TEM picture of Comparative Example 2 showing aggregation.

Zinc oxide was obtained in the same manner as shown in Example 8 except that the agitation was at 500 rpm and the addition of the alkali was made over a period of 7 minutes. Aggregation was observed with the use of a TEM as shown in FIG. 6. The particles had a size of 1.5 micron on the average, UV absorption of 43 percent and a loose bulk specific volume of 3 cc/g.

The flaky zinc oxide particles prepared in Examples 1 to 17 were subjected to organoleptic tests in comparison with a comparative product and exhibited a far better spreadability, less squeak and higher transparency. When they were applied to the skin, the white color of them disappeared in a quite short time.

EXAMPLE 18 (POWDERY FOUNDATION)

A powdery foundation having the following composition was prepared by the following process:

| Composition | |
| --- | --- |
| (1) mica | the balance |
| (2) flaky zinc oxide prepared in Example 1 | 10 wt. % |
| (3) talc | 20 |
| (4) titanium oxide | 10 |
| (5) red iron oxide | 0.8 |
| (6) yellow iron oxide | 2.5 |
| (7) black iron oxide | 0.1 |
| (8) liquid paraffin | 8 |
| (9) beeswax | 2 |
| (10) antiseptic | a suitable amount |
| (11) perfume | a minute amount |

Preparation

The components (1) to (7) were mixed together and pulverized. The powder was placed in a highperformance blender. A solution prepared by mixing the components (8) to (10) at 80° C. was added thereto and homogeneously mixed. The component (11) was added to the mixture, mixed, pulverized again and passed through a sieve. The powder thus formed was compression-molded in a metallic pan.

COMPARATIVE EXAMPLE 5

A powdery foundation was prepared in the same manner as that of Example 18 except that the flaky zinc oxide produced in Example 1 was replaced with the comparative one.

As compared with the powdery foundation produced in Comparative Example 5, that prepared in Example 18 had a superior touch, i.e. spreadability or freeness from squeak and a natural makeup was possible with it.

EXAMPLE 19

Powdery foundations were prepared in the same manner as that of Example 18 except that the flaky zinc oxide prepared in Example 1 was replaced with flaky zinc oxide prepared in each of Examples 2 to 7.

The powdery foundations thus prepared had excellent spreadability and were free from squeaky touch and a natural makeup was possible with it like that prepared in Example 18.

EXAMPLE 20 (CREAMY FOUNDATION)

A creamy foundation having the following composition was prepared by the following process:

| Composition | |
|---|---|
| (1) stearic acid | 5 wt. % |
| (2) lipophilic glycerol monostearate | 2.5 |
| (3) cetostearyl alcohol | 1 |
| (4) propylene glycol monolaurate | 3 |
| (5) squalane | 7 |
| (6) olive oil | 8 |
| (7) purified water | the balance |
| (8) antiseptic | a suitable amount |
| (9) triethanolamine | 1.2 |
| (10) sorbitol | 3 |
| (11) titanium oxide | 10 |
| (12) talc | 5 |
| (13) coloring pigment | a suitable amount |
| (14) flaky zinc oxide prepared in Example 1 | 8 |
| (15) perfume | a minute amount |

Preparation

The components (11) to (14) were mixed together and pulverized. Separately, aqueous components (7) to (10) were mixed together to form a solution. The pulverized pigment mixture was dispersed in the solution and a dispersion thus formed was heated to 75° C. A mixture of oily components (1) to (6) was heated to 80° C. to form a solution, which was added to the aqueous dispersion prepared as above under stirring to form an emulsion. The emulsion was cooled under stirring to 50° C. and the component (15) was added thereto. The mixture was cooled under stirring.

COMPARATIVE EXAMPLE 7

A creamy foundation was prepared in the same manner as that of Example 20 except that the flaky zinc oxide prepared in Example 1 was replaced with a comparative one.

Unlike the creamy foundation prepared in Comparative Example 7, the creamy foundation prepared in Example 20 was free from squeaky touch and a natural makeup was possible with it.

EXAMPLE 21

Creamy foundations were prepared in the same manner as that of Example 20 except that the flaky zinc oxide prepared in Example 1 was replaced with flaky zinc oxide prepared in each of Examples 2 to 7.

The creamy foundations thus prepared were free from squeaky touch and a natural makeup was possible with it like the creamy foundation prepared in Example 20.

EXAMPLE 22 (OILY FOUNDATION)

An oily foundation having the following composition was prepared by the following process:

| Composition | |
|---|---|
| (1) flaky zinc oxide prepared in Example 1 | 10 wt. % |
| (2) talc | the balance |
| (3) kaolin | 12 |
| (4) titanium oxide | 13 |
| (5) red iron oxide | 1.5 |
| (6) yellow iron oxide | 2.0 |
| (7) black iron oxide | 0.5 |
| (8) liquid paraffin | 15 |
| (9) isopropyl palmitate | 10 |
| (10) lanolin alcohol | 3 |
| (11) microcrystalline wax | 7 |
| (12) ozocerite | 8 |
| (13) antiseptic | a suitable amount |
| (14) perfume | a suitable amount |

Preparation

The components (1) to (7) were mixed together and pulverized. The powder was slowly added to an oily solution prepared by heating the components (8) to (13) at 80° C. and then dispersed homogeneously. The component (14) was added to the dispersion and the mixture thus formed was packed in a metallic pan and cooled.

COMPARATIVE EXAMPLE 8

An oily foundation was prepared in the same manner as that of Example 22 except that the flaky zinc oxide prepared in Example 1 was replaced with the comparative one.

As compared with the oily foundation prepared in Comparative Example 8, the oily foundation prepared in Example 22 was free from squeaky touch and a natural makeup was possible with it.

EXAMPLE 23

Oily foundations were prepared in the same manner as that of Example 22 except that the flaky zinc oxide prepared in Example 1 was replaced with the flaky zinc oxide prepared in each of Examples 2 to 7.

The oily foundations thus prepared were free from squeaky touch and a natural makeup was possilbe with it like that prepared in Example 22.

EXAMPLE 24 (O/W TYPE CREAM)

An O/W-type cream having the following composition was prepared by the following process:

| Composition | |
|---|---|
| (1) beeswax | 5.5 wt. % |
| (2) cetanol | 4.5 |
| (3) hydrogenated lanolin | 7 |
| (4) squalane | 33 |
| (5) glycerol fatty acid ester | 3.5 |
| (6) lipophilic glycerol monostearate | 2 |
| (7) polyoxyethylene (EO 20) sorbitan monolaurate | 2 |
| (8) flaky zinc oxide prepared in Preparation Example 1 | 8 |

| Composition | |
| --- | --- |
| (9) perfume | a minute amount |
| (10) antiseptic | a suitable amount |
| (11) antioxidant | a suitable amount |
| (12) propylene glycol | 4.5 |
| (13) purified water | a suitable amount |

Preparation

The components (8), (10), (12) and (13) were stirred together to form a mixture, which was kept at 80° C. to form an aqueous solution. Other components were mixed therein and the mixture was heated at 80° C. to form an oily solution. The aqueous solution was added to the oily solution and the mixture thus obtained was pre-emulsified and then homogeneously emulsified with a homomixer. The emulsion was cooled to 30° C. to obtain a product.

COMPARATIVE EXAMPLE 9

An O/W-type cream was prepared in the same manner as that of Example 24 except that the flaky zinc oxide prepared in Example 1 was replaced with a comparative one.

The cream thus prepared was substantially free from squeaky touch and had an excellent touch and a natural makeup was possible with it, while when the cream prepared in Comparative Example 9 was applied to the skin, an unnatural white makeup was obtained.

EXAMPLE 25

O/W-type creams were prepared in the same manner as that of Example 24 except that the flaky zinc oxide prepared in Example 1 was replaced with the flaky zinc oxide prepared in each of Examples 2 to 7.

The O/W-type creams thus prepared were substantially free from squeaky touch, had an excellent touch and a natural makeup was possible with them like that prepared in Example 22.

We claim:

1. Zinc oxide particles having an average particle diameter of 0.1 to 1 micron, an average particle thickness of 0.01 to 0.2 micron and a mean platy ratio of at least 3.

2. A process for preparing zinc oxide particles having an average particle diameter of 0.1 to 1 micron, an average particle thickness of 0.01 to 0.2 micron and a mean platy ratio of at least 3, comprising the steps of forming precipitates of zinc oxide, at a reaction temperature of 60° C. or lower, in a solution which (a) contains zinc ions, (b) contains one or more acid radicals in a total amount exceeding the equivalent with respect to the zinc ions and (c) has a pH of 11 or higher, and separating the precipitates from the solution.

3. A process as claimed in claim 2, in which the formation of precipitates is conducted in the presence of a watersoluble organic substance.

4. A process for preparing zinc oxide particles having an average particle diameter of 0.1 to 1 micron, an average particle thickness of 0.01 to 0.2 micron and a mean platy ratio of at least 3, comprising the steps of mixing an aqueous solution of a zinc salt with a solution of a precipitating agent, agitating the mixed solutions and forming precipitates of zinc oxide, at a reaction temperature of 60° C. or lower, in a solution of the mixed solutions having (a) a zinc salt content of from 0.1 to 15 wt. % and (b) a pH of 11 or larger.

5. A process as claimed in claim 4, in which the formation of precipitates is in the presence of a watersoluble organic substance.

6. A zinc oxide composition for external application to the human body comprising zinc oxide particles having an average particle diameter of 0.1 to 1 micron, an average particle thickness of 0.01 to 0.2 micron and a mean platy ratio of at least 3.

7. A composition as claimed in claim 6, which comprises 0.1 to 50 wt. % of the particles of zinc oxide.

* * * * *